United States Patent
Fitzgerald

(10) Patent No.: US 9,228,979 B2
(45) Date of Patent: Jan. 5, 2016

(54) CAPACITIVE TRANSIMPEDANCE AMPLIFIER WITH OFFSET

(71) Applicant: Smiths Detection-Watford Limited, Watford (GB)

(72) Inventor: John Patrick Fitzgerald, Watford (GB)

(73) Assignee: Smiths Detection-Watford Limited (GB)

( * ) Notice: Subject to any disclaimer, the term of this patent is extended or adjusted under 35 U.S.C. 154(b) by 0 days.

(21) Appl. No.: 14/401,277

(22) PCT Filed: May 31, 2013

(86) PCT No.: PCT/GB2013/051460
§ 371 (c)(1),
(2) Date: Nov. 14, 2014

(87) PCT Pub. No.: WO2013/179058
PCT Pub. Date: Dec. 5, 2013

(65) Prior Publication Data
US 2015/0136965 A1    May 21, 2015

Related U.S. Application Data

(60) Provisional application No. 61/654,426, filed on Jun. 1, 2012.

(51) Int. Cl.
*H01J 49/02* (2006.01)
*H03F 1/08* (2006.01)
*G01N 27/62* (2006.01)
*H03F 3/70* (2006.01)

(52) U.S. Cl.
CPC ............ *G01N 27/622* (2013.01); *H01J 49/022* (2013.01); *H03F 3/70* (2013.01); *H03F 2200/267* (2013.01)

(58) Field of Classification Search
CPC ......... H01J 49/022; H01J 49/025; H03F 1/08; H03F 1/26; G01F 23/266; G01N 27/228; G01R 19/0023; G01R 19/255
USPC .......... 250/281, 283, 397, 343, 214 A, 338.4; 324/658, 665
See application file for complete search history.

(56) References Cited

U.S. PATENT DOCUMENTS

| | | | |
|---|---|---|---|
| 4,442,349 A * | 4/1984 | Blom et al. ................. | 250/222.1 |
| 4,542,295 A * | 9/1985 | Mattson et al. ............... | 250/352 |
| 4,620,148 A * | 10/1986 | Davison et al. ............. | 324/99 D |
| 5,012,202 A | 4/1991 | Taylor | |
| 6,028,312 A * | 2/2000 | Wadsworth et al. .......... | 250/351 |
| 6,064,066 A * | 5/2000 | Bevan et al. .................. | 250/345 |
| 6,444,970 B1 * | 9/2002 | Barbato .................... | 250/214 A |
| 6,731,121 B1 | 5/2004 | Hsu et al. | |
| 6,809,313 B1 * | 10/2004 | Gresham et al. .............. | 250/287 |

(Continued)

FOREIGN PATENT DOCUMENTS

WO    2009091999    7/2009

*Primary Examiner* — David A Vanore
(74) *Attorney, Agent, or Firm* — Advent LLP

(57) ABSTRACT

Spectrometers including integrated capacitive detectors are described. An integrated capacitive detector integrates ion current from the collector (768) into a changing voltage. The detector includes a collector configured to receive ions in the spectrometer, a dielectric, and a plate arranged in an overlapping configuration with collector on an opposite side of the dielectric. The detector also includes an amplifier (764). A capacitive detector with offset (776) is described.

20 Claims, 6 Drawing Sheets

(56) References Cited

U.S. PATENT DOCUMENTS 7,145,350 B2 * 12/2006 Mellert et al. ............... 324/678
7,403,065 B1 * 7/2008 Gresham et al. ............... 330/9
2013/0284914 A1 * 10/2013 Zaleski et al. ............... 250/282
2013/0298938 A1 * 11/2013 Bian et al. ............... 134/1
2015/0129756 A1 * 5/2015 Fitzgerald ............... 250/281
2015/0136965 A1 * 5/2015 Fitzgerald ............... 250/281

* cited by examiner

CAPACITIVE TRANSIMPEDANCE AMPLIFIER WITH OFFSET

BACKGROUND OF THE INVENTION

Field of the Invention

The present disclosure relates to a detector apparatus and more particularly to detectors for spectrometers.

Ion mobility spectrometers ("IMS") and field asymmetric ion mobility spectrometers ("FAIMS") or differential mobility spectrometers ("DMS") apparatus are often used to detect substances such as explosives, drugs, blister and nerve agents or the like. A spectrometer typically includes a detector cell to which a sample of air containing a suspected substance or analyte is supplied as a gas or vapor. The cell operates at or near atmospheric pressure and contains electrodes energized to produce a voltage gradient along the cell.

Molecules in the sample of air are ionized, such as by means of a radioactive source, an ultraviolet ("UV") source, or by corona discharge, and are admitted into the drift region of the cell by an electrostatic gate at one end. The ionized molecules drift to the opposite end of the cell at a speed dependent on the size of the ion to a collector, which causes a current pulse in the collector. The current into the collector is converted to a voltage and amplified. By measuring the time of flight along the cell it is possible to identify the ion.

The subject matter discussed in this background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

SUMMARY OF THE INVENTION

Spectrometers including capacitive detectors with offsets are described. The spectrometers can be used to ionize molecules from a sample of interest in order to identify the molecules based on the ions. In an implementation, the ions drift along a chamber within a spectrometer and are collected by a collector. The ion signal produced is amplified by a transimpedance amplifier. A capacitor is disposed in a feedback loop of the transimpedance amplifier. This circuit is configured to act as an integrator. The output of the circuit is connected to a measuring system.

In one aspect, a spectrometer is provided. The spectrometer includes a detector. The detector includes a collector configured to detect ions and a capacitive transimpedance amplifier coupled to the collector. The spectrometer also includes an offset circuit coupled to the capacitive transimpedance amplifier included in the detector.

In another aspect, a spectrometer is provided. The spectrometer includes a detector. The detector includes an amplifier including an input and an output. The output is coupled with a capacitor. The detector also includes a collector coupled with the input of the amplifier configured to collect ions that contact the collector. The detector also includes an offset circuit coupled with the amplifier.

In another aspect, a spectrometer is provided. The spectrometer includes a collector configured to receive ions coupled with a summing junction. The spectrometer also includes summing junction. The summing junction is coupled to an input of an amplifier including an input and an output, the amplifier also having an output. The spectrometer also includes an offset circuit including an input and an output. The input is coupled with the output of the amplifier. The spectrometer also includes a capacitor coupled with the output of the offset circuit and with the summing junction.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION OF AN EXEMPLARY EMBODIMENTS

Figure 1:
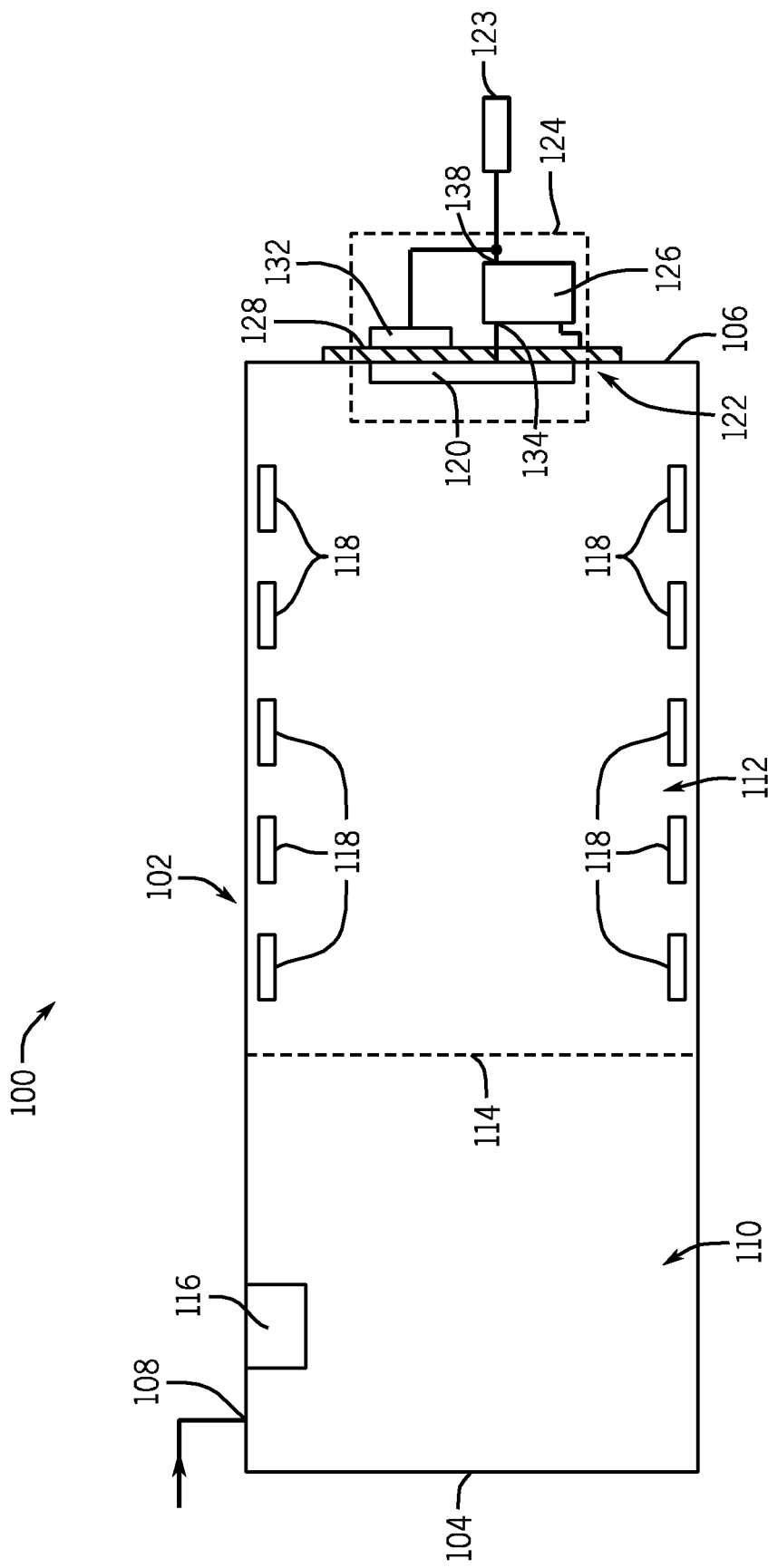
FIG. 1 is a schematic illustration of an exemplary IMS apparatus including an integrated capacitive detector in accordance with an embodiment of this disclosure.

FIG. 1 is a schematic illustration of an exemplary spectrometer, such as an ion mobility spectrometer ("IMS") 100 that implements electrical ionization of molecules in a sample of interest. The IMS 100 includes an elongate housing 102 extending from a first wall 104 to a second wall 106. Defined in the housing 102 proximate the first wall 104 is an inlet 108. Molecules of interest may be drawn into the housing 102 through the inlet 108. The housing 102 also defines an ionization chamber 110 and a drift chamber 112 in fluid communication but separated by a gate 114 that can control passage of ions to the drift chamber 112. The ionization chamber 110 includes an ionization source 116, which may be a radioactive source, such as a nickel 63 source, a corona discharge device, a photoionization source, or any other suitable type of source for ionizing the sample of interest. The drift chamber 112 includes electrode pairs 118 spaced along the drift chamber 112 to provide a potential gradient along the length of the drift chamber 112 that is effective to draw ions from left to right (as shown in FIG. 1). Proximate the second wall 106 of the housing 102 in the drift chamber 112 is a collector 120 of a detector 122. Ions are detected as the ions come in contact with the collector 120.

Ionization of the molecules of interest can occur in a variety of ways. For example, an ionization source can ionize a molecule through various multistep processes using ions that are formed in the plasma.

In embodiments, reactant ions are generated by a corona. The reactant ions ionize the molecule of interest. For example, the ionization source forms ions that are subsequently drawn away to ionize the molecules of interest. Reactant ions may be ionized gases (e.g., nitrogen and gases in air) and other gases in the ionization chamber, such as water, and so forth. Although fragmentation of the molecule of interest is possible, ionization can be controlled to result in "soft" ionization thereby minimizing fragmentation of the molecule in favor of the molecule carrying a single charge, e.g., a plus one or minus one charge.

In one embodiment, the IMS times how long it takes an ion to reach the collector 120 after the gate 114 is opened. This time-of-flight can be associated with the underlying molecule. The ion's ion mobility is used to identify the molecule associated with the ion. For example, a computer can be used to compare the detector's 122 output with a library of plasmagrams of known ions. The ion current discharged from the collector 120 is typically very small. Therefore, as will be described further below, the detector 122 includes an amplification circuit 124 including an amplification element 126 to amplify the ion current. The output of the detector 122 may be coupled to a measuring system 123, as will be discussed further below.

Embodiments of measuring systems 123 may include analog-to-digital converters, digital-to-analog converters, amplification elements, processors, etc., as will be further explained below. Processors are not limited by the materials from which they are formed or the processing mechanisms employed therein. For example, the processor may be comprised of semiconductor(s) and/or transistors (e.g., electronic integrated circuits ("IC's")). Memory can be included with the processor. Memory can store data, such as a program of instructions for operating the IMS, data, and so on. Although a single memory device can be used, a wide variety of types and combinations of memory (e.g., tangible memory) may be employed, such as random access memory ("RAM"), hard disk memory, removable medium memory, external memory, and other types of computer-readable storage media. Embodiments may include other suitable measuring systems.

Ions move down the drift chamber 112 towards the second wall 106. Located proximate the second wall 106 is the collector 120. In the illustrated embodiment, the collector 120 is supported by a dielectric 128. The dielectric 128 may be any suitable dielectric, and in the illustrated embodiment is a printed circuit board ("PCB") composed of polyimide. The collector 120 may be composed of any suitable material (e.g., copper, other metals, conductive materials, etc.) or combination of materials and may be deposited on the PCB or coupled with the PCB by suitable means.

Figure 2:
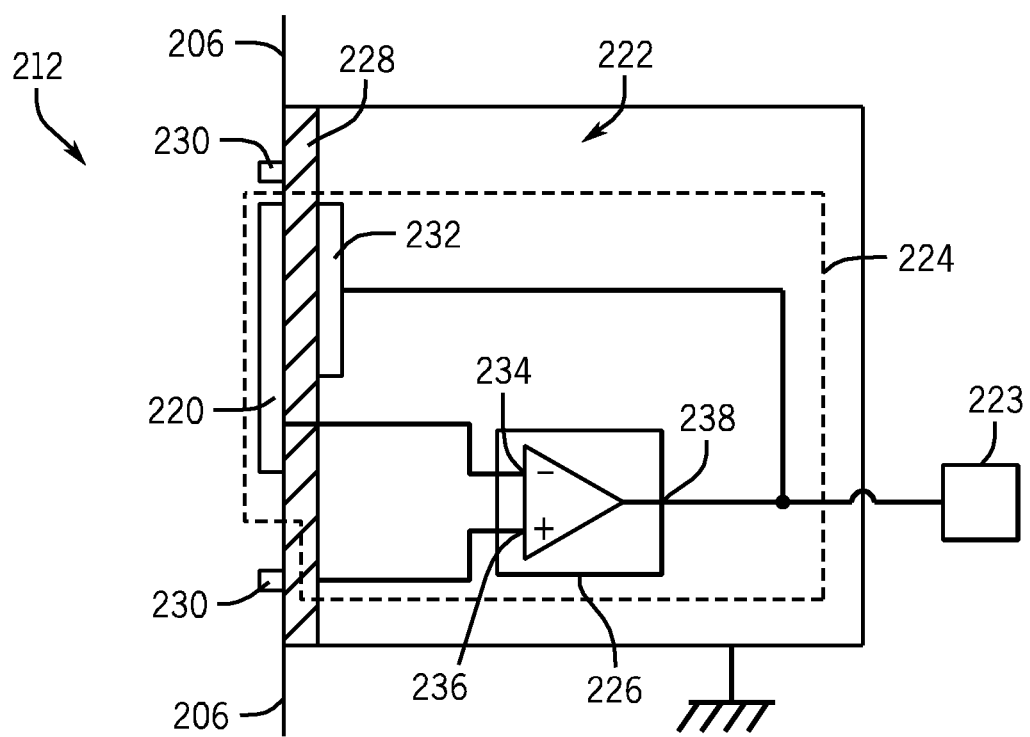
FIG. 2 illustrates a detailed view of an embodiment of an integrated capacitive detector that may be utilized, for example, as an integrated capacity detector with the exemplary IMS apparatus illustrated in FIG. 1.

FIG. 2 illustrates a detailed view of an embodiment of an integrated capacitive detector that may be utilized, for example, as an integrated capacity detector with the exemplary IMS apparatus illustrated in FIG. 1. The collector 220 is deposited on the PCB 228 over a suitable area for collecting ions. In one embodiment the PCB 228 is substantially circular with a diameter of approximately 7.5 millimeters and a square area of approximately 44 square millimeters. Other suitable shapes, dimensions, and areas are also envisioned. In one embodiment, the collector 220 is of a size that is sufficiently compact while permitting accurate detection. In the illustrated embodiment, the collector 220 is surrounded by a guard ring 230. The guard ring 230 may be formed from any suitable material.

Supported on the side of the PCB 228 opposite the collector 220 is a capacitive plate element 232. The capacitive plate element 232 may be composed of any suitable material (e.g., copper, other metals, etc.) or combination of materials and may be deposited on the PCB or coupled with the PCB by any suitable means.

A parallel plate capacitor has a capacitance based on the overlapping surface area of the plates, the separation between the plates, and the dielectric constant (relative permittivity) according to the equation $$C = (k * 8.854 * 10^{-12} * A/D) * 1 * 10^{-12}$$

where k is the dielectric constant of the dielectric material, A is the overlapping area of the plates, D is the distance between the plates, and C is the capacitance of the capacitor.

The overlapping portions of the capacitive plate element 232 and the collector 220, along with the PCB 228 are configured to act as a capacitor, with the portion of the collector 220 overlapping the capacitive plate element 232 acting as one of the plates of a capacitor and the PCB 228 acting as the dielectric, and the capacitive plate element 232 acting as the other plate of a capacitor. The capacitive plate element 232 is dimensioned to have an area overlapping a portion of the area of the collector 220 to achieve a desired capacitance for a desired application, as will be further described below. In one embodiment, the PCB 228 is formed from polyimide, which has a dielectric constant of approximately 3.4. The capacitive plate element 232 is sized to have approximately 44 square millimeters of area overlapping the collector 220. The PCB 228 is approximately 1.5 millimeters thick. Thus, the capacitance of the capacitor formed by the collector 220, the capacitive plate element 232, and the PCB 228 is approximately 0.883 picoFarads. Other arrangements resulting in other capacitances suitable for various applications are also envisioned.

As will be explained further below, the capacitor formed by the overlapping portions of the capacitive plate element 232 and the collector 120 along with the dielectric and the collector 220 form a summing junction node of a capacitive transimpedance amplifier circuit. This summing junction node is coupled with a first input 234 of the amplification element 226.

With further reference to FIG. 2, the amplification element 226 is an operation amplifier of any suitable type. Additionally, other suitable types of amplification elements are also envisioned. The first input 234 of the operational amplifier 226 is its inverting input. The operational amplifier 226 also includes a second input 236, which is the non-inverting input of the operational amplifier 226. The second input 236 of the operational amplifier 226 is grounded. The operational amplifier 226 also includes an output 238. The output 238 is coupled with the capacitive plate element 232.

Figure 3:
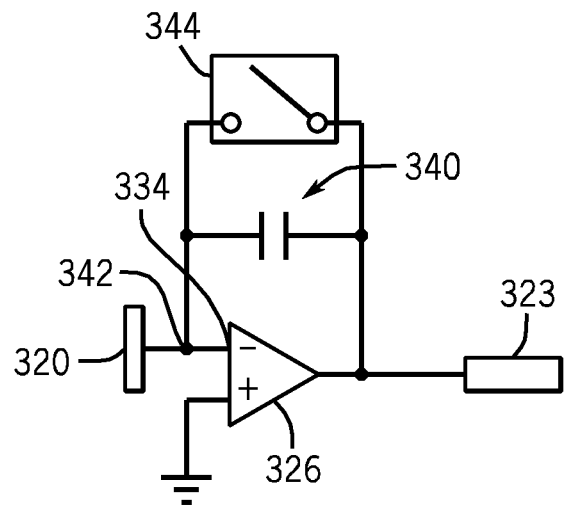
FIG. 3 is a schematic illustration of an embodiment of a transimpedance amplifier circuit, such as, for example, a circuit formed by the arrangement illustrated in FIG. 2.

FIG. 3 is a schematic illustration of the circuit formed by the apparatus illustrated in FIG. 2. The capacitor formed by the capacitive plate element 232, the dielectric 228, and the collector 229 of FIG. 2 functions as a feedback capacitor 340 disposed in a feedback loop of the amplification element 326. The feedback capacitor 340 and the collector 320 meet at a summing junction node 342 which is coupled with the inverting input 334 of the operational amplifier 326.

The circuit of FIG. 3 functions as a capacitive transimpedance amplifier that converts current applied to its input to a low impedance output. As ions impact the collector 320, this ion signal causes charge to accumulate across the capacitor 340 and the output of the operational amplifier 326 increases in the positive or negative direction dependent on the polarity of the input signal. Thus, the circuit, as illustrated, operates as an integrator and integrates the ion current from the collector 320 as an increasing voltage.

As the charge accumulates on the capacitor 340, the capacitor 340 may reach its operational limit, requiring discharging to reset the capacitor 340. In one embodiment, the capacitor 340 is coupled in parallel with a resetting switching circuit 344. When it is desired to reset the capacitor 340, the switch of the resetting switching circuit 344 may be closed, allowing the capacitor 340 to be reset and discharge. In embodiments, the resetting switching circuit 344 may also contain resistive elements to control the rate of change of voltage to limit instantaneous current and so forth.

Figure 4:
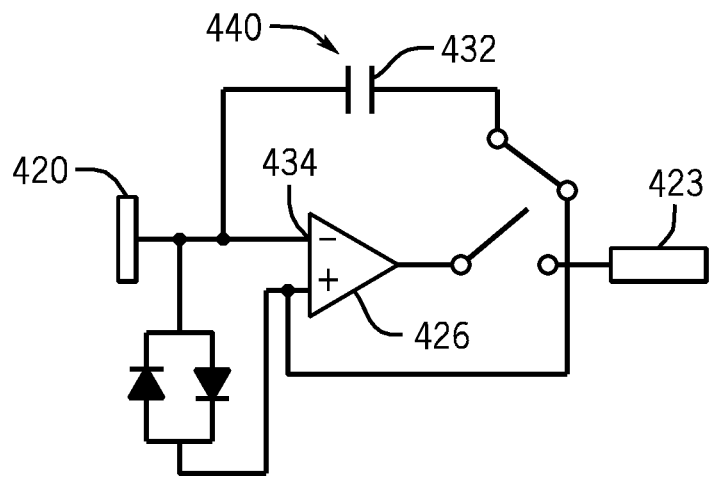
FIG. 4 is a schematic illustration of an alternate embodiment of the circuit formed by the arrangement illustrated in FIG. 2.

FIG. 4 is a schematic illustration of the circuit formed by the apparatus illustrated in FIG. 2 with an alternate arrangement for discharging the capacitor 440. Various operational amplifiers 426 provide input protection diodes. The capacitive plate element 432 which is coupled with the output of the operational amplifier 426 is switched to be grounded. Charge stored on the capacitor is then dissipated through the protection diodes of the operational amplifier 426. In some embodiments resistive elements are provided to limit instantaneous current during discharge.

The operational amplifier 426 includes supply connections to provide power to the operational amplifier 426. The capacitor 440 is reset, in some examples, by grounding the supply connections of the operational amplifier 426. Charge stored on the capacitor 440 is then dissipated through the internal diode structures of the operational amplifier.

In another embodiment the capacitor 440 is reset by partially or fully reversing the supply connections of the operational amplifier 426. Charge stored on the capacitor 440 is then dissipated through the internal diode structures of the operational amplifier. In some embodiments resistive elements are incorporated to control the rate of change of voltage to limit instantaneous current.

In still another embodiment, the spectrometer 100 further includes ion generators in switched polarity cells. Instead of resetting the capacitor 440, the ion generators are used to swing the capacitor to the opposite polarity.

Figure 5:
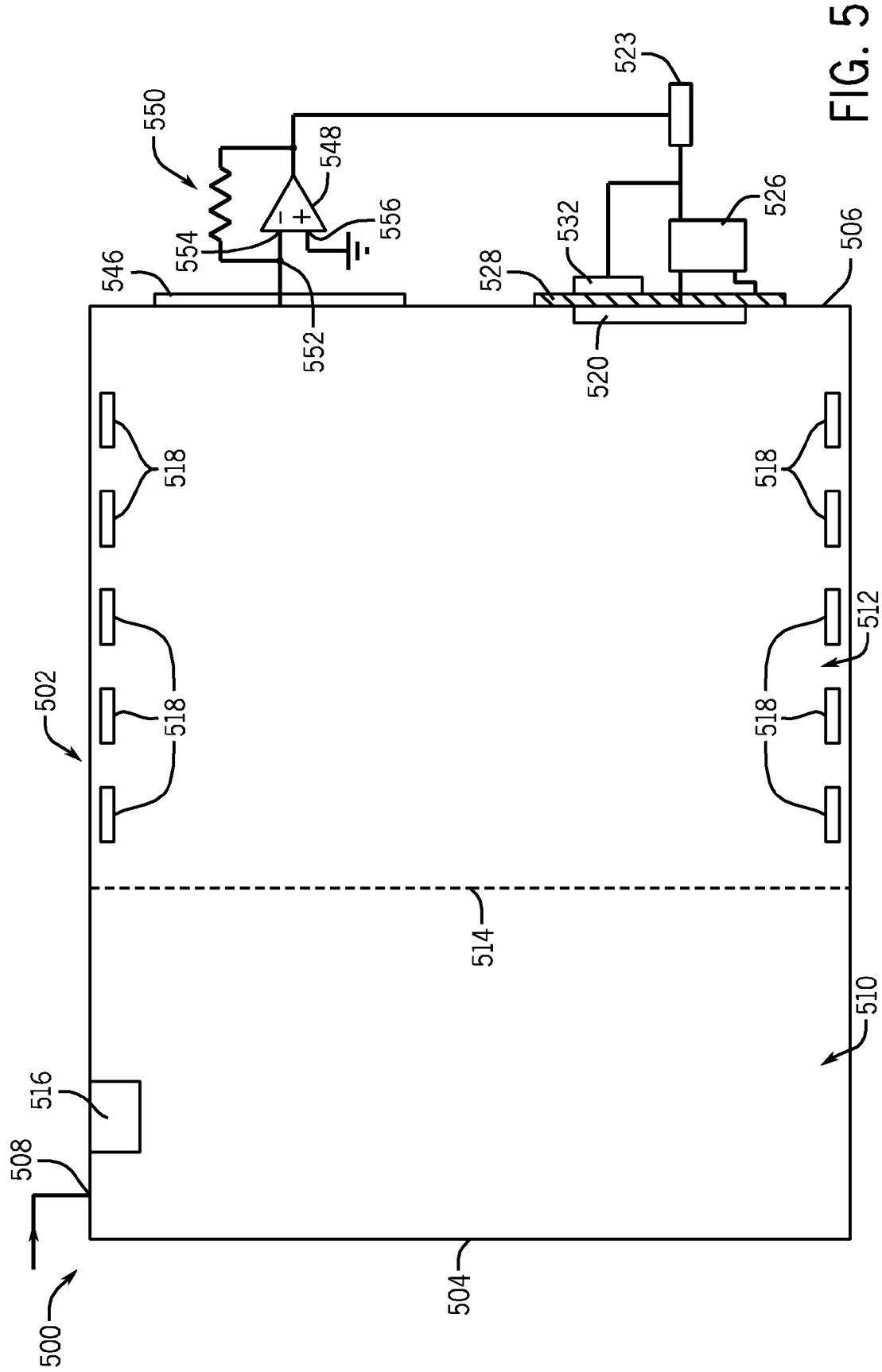
FIG. 5 is a schematic illustration of a second embodiment of an IMS apparatus including an integrated capacitive detector and a second detector.

FIG. 5 illustrates an alternate embodiment of a spectrometer 500. The spectrometer 500 includes substantially the same components as the spectrometer 100 of FIG. 1, however, the spectrometer 500 also includes a second collector 546, a second operational amplifier 548 and a resistive element 550 disposed in a feedback loop of the operational amplifier 548. The resistive element 550 and the second collector 546 are coupled at a junction 552 which is coupled with the inverting input 554 of the second operational amplifier 548. The non-inverting input 556 of the second operational amplifier 548 is grounded.

In operation in this embodiment, a sample of interest is drawn into the ionization chamber 510 and the ionization source 516 ionizes the sample. For a first portion of time subsequent to the gate 514 being opened allowing ions to travel through the drift chamber 512, the ions are collected by the second collector 546. During this period of time, the first collector 520 and its related circuitry are held in a reset state. Ionization by the ionization source 516 typically results in a reactant ion peak (and resultant reactant ion peak current). Until this reactant ion peak has passed, the second collector 546 and its associated circuitry can be used. However, after the reactant ion peak, the first collector 520 and its related circuitry are no longer held to reset and are used to monitor the ion stream either alone or in combination with the second collector 546. The described arrangement may be used in this way to magnify selected portions of the ion spectrum.

Figure 6:
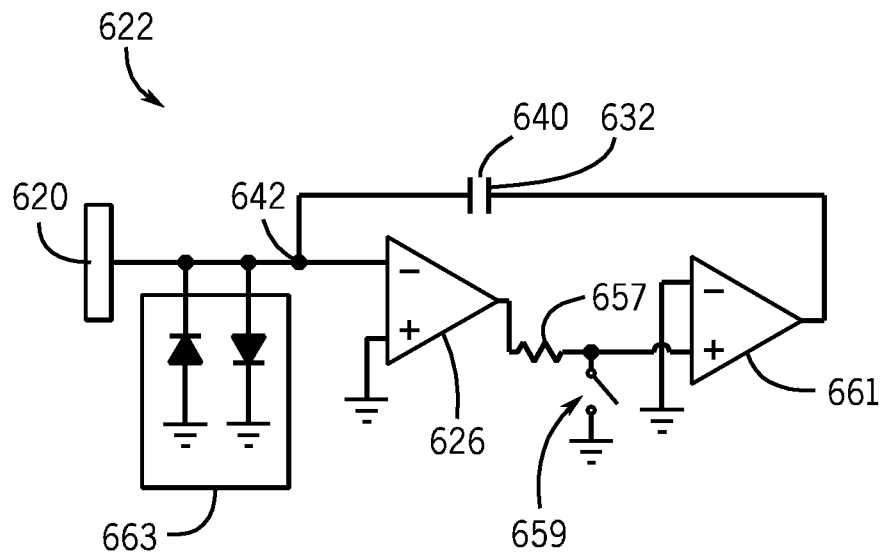
FIG. 6 is a schematic illustration of an embodiment of a detector with a reset circuit.

FIG. 6 illustrates an alternate embodiment of a detector 622. In this embodiment, the output of operational amplifier 626 is coupled with a resistive element 657. The resistive element 657 is coupled with a switch 659 that, when closed, grounds the resistive element 657. When the switch 659 is open, the resistive element 657 is coupled with the non-inverting input of a second amplification element 661, In one embodiment an instrumentation amplifier. The output of the second operational amplifier 661 is coupled with the feedback capacitor 640. Based on this configuration, the charge across the feedback capacitor 640 can be changed independently of the existing state of the system and independently of the input signal. When the switch 659 is closed, the voltage at the capacitive plate element 632 connected to the second amplification element 661 can be driven to any level within the supply voltages of the amplification element. The opposite plate of the capacitor 640 is held near ground by back-to-back diodes 663. While the diodes 663 are shown as separate elements, In one embodiment, these diodes 663 are incorporated into the input circuit of the first amplification element 626. Thus, In one embodiment, the capacitor 640 may be reset without additional components or additional connections to the summing junction node 642.

It is envisioned that embodiments of capacitive detectors may be used without being reset, for example, by using offset features. One example of a detector with which it is envisioned that embodiments of the present invention could be used is disclosed in U.S. Patent Application No. 61/654,333, entitled Integrated Capacitor Transimpedance Amplifier, which was filed concurrently with and assigned to the assignee of the present application, incorporated herein by reference in its entirety. Additionally, it is also envisioned that embodiments of the present invention may be used with any suitable spectrometer apparatus, including those in which the collector does not form a part of a capacitor or store charge (e.g., separate capacitor).

Figure 7:
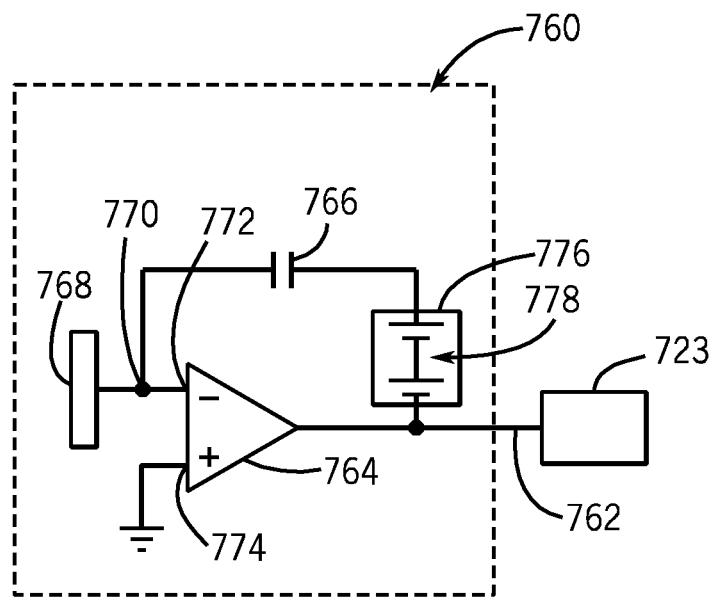
FIG. 7 is a schematic illustration of an embodiment of a detector including an offset circuit.

With reference to FIG. 7, an embodiment of a capacitive detector with offset 760 is illustrated. In this embodiment, the output 762 of the detector 760 is coupled with a measuring system 723. In one embodiment, the measuring system 723 includes an analog-to-digital converter of any suitable type. In the illustrated embodiment, the detector 760 is configured to function as an integrator driven by the ion signal from an ion mobility spectrometer.

The detector 760 includes an operational amplification element 764, In one embodiment, an operational amplifier, and a capacitor 766. The capacitor 766 is coupled with the output of a collector 768 at a summing junction 770, which is coupled with the inverting input 772 of the operational amplifier 764. The non-inverting input 774 of the operational amplifier 764 is grounded. The capacitor 766 is also coupled with an offset circuit 776. The offset circuit 776 is connected with the output of the operational amplifier 764.

In operation, the detector 760 operates as an integrator with the ion signal from a spectrometry apparatus collected by the collector 768 driving the integrator. The ion signal causes charge to accumulate across the capacitor 766 and the output of the operational amplifier 764 increases in the positive or negative direction dependent on the polarity of the input signal.

In some systems, the available output of operational amplifiers may be limited by their supply voltage. Additionally, measuring systems 723 or components thereof may have may have limited input range. Thus, an input signal from the collector 768 of a single polarity may cause the output of the operational amplifier 764 to reach its limit or to reach the limit of the input range of the measuring system 723 or a component thereof.

The offset circuit 776 offsets the output signal so that the output of the operational amplifier 764 is returned within its limit and the limit of the input range of the measuring system 723. Thus, the input range of the measuring system may be reused, if each time the output signal of the operational amplifier 764 goes out of range it is offset by the input range of the measuring system 723.

In the embodiment illustrated in FIG. 7, the measuring system 723 includes an analog-to-digital converter with a limited input range. The offset circuit 776 in the embodiment illustrated in FIG. 7 includes a voltage source 778. The voltage source 778 selectively generates voltage so when the output voltage of the operational amplifier 764 goes above a preset limit, the voltage source 778 generates voltage to offset the output voltage and return the output of the operational amplifier back within its limits and the output 762 of the detector 760 within the input range of the measuring system 723.

Figure 8:
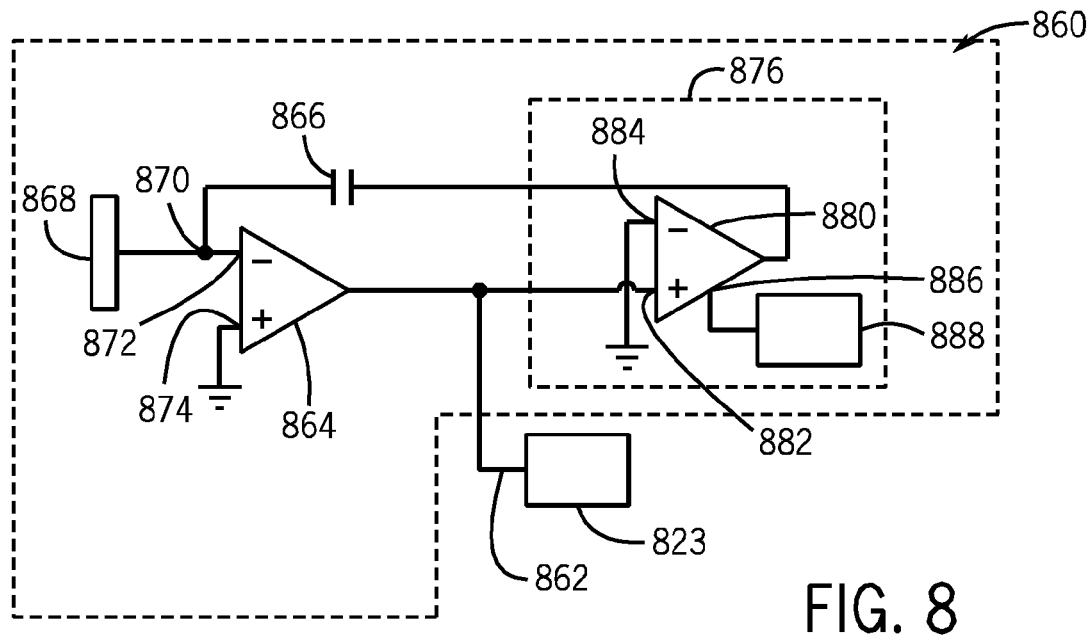
FIG. 8 is a schematic illustration of another embodiment of a detector including an offset circuit.

FIG. 8 illustrates another embodiment of a capacitive detector with offset 860. In this embodiment, the offset circuit 876 includes a second amplification element 880 such as an instrumentation amplifier. Other suitable amplification elements include, but are not limited to, integrated circuit instrumentation amplifiers or instrumentation amplifiers formed from various components, or the like. The output of the operational amplifier 864 is coupled with the non-inverting input 882 of the instrumentation amplifier 880. The inverting input 884 is grounded. The instrumentation amplifier 880 also includes a reference voltage input 886 coupled with a selectively variable reference voltage source 888.

By varying the voltage output by the selectively variable reference voltage source 888, the output of the instrumentation amplifier 880 and of the detector 860 can be varied. Thus, when the output limit of the operational amplifier 864 would be reached, adjustment of the output of the voltage source 888 can be used to extend the dynamic range of the detector 860.

Figure 9:
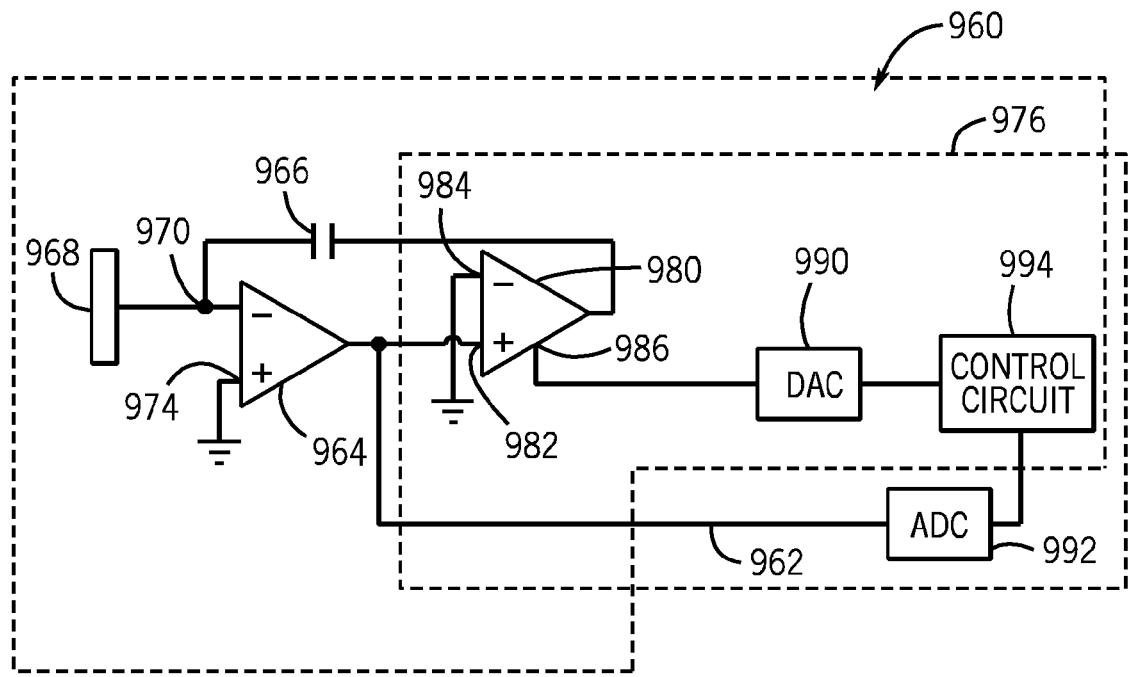
FIG. 9 is a schematic illustration of another embodiment of a detector including an offset circuit.

FIG. 9 illustrates another embodiment of a capacitive detector with offset 960. In this embodiment, the reference voltage input 986 of the instrumentation amplifier 980 is coupled with a digital-to-analog converter 990. The output 962 of the detector 960 is coupled with an analog-to-digital converter 992 which in turn is coupled with a control circuit 994, such as a processor. The control circuit 994 is coupled with the digital-to-analog converter 990. Thus, the control circuit 994 receives a signal based on the output 962 of the detector 960 and is configured to provide an input to control the amplification of the instrumentation amplifier 980. Control of the instrumentation amplifier 980 may In one embodiment be based on the output signal of the detector 960, programmed logic, or any other suitable control. In one embodiment, selective control of the offset by the control circuit 994 can be commanded at any time.

In one embodiment, the analog-to-digital converter 992, the control circuit 994, and the digital-to-analog converter 990 may be combined in a microcontroller.

In another embodiment utilizing an integrated capacitive transimpedance amplifier, such as that described in U.S. Patent Application No. 61/654,333, entitled Integrated Capacitor Transimpedance Amplifier, which was filed concurrently with and assigned to the assignee of the present application, that the analog-to-digital converter 992, the control circuit 994, and the digital-to-analog converter 990 may be integrated with and supported by the dielectric described therein. Additionally, the collector described in the Integrated Capacitor Transimpedance Amplifier may act as a plate of the capacitor of the capacitive detectors with offset described above and illustrated in the figures herein.

Thus, it may be seen that embodiments of a capacitive detector with offset as described may allow for wide dynamic range limited only by the capacitor's voltage rating and the limits of a second amplification element, while keeping other levels in the arrangement within normal limits. Embodiments of a capacitive detector with offset as described may provide wide dynamic system range despite supply and output limits of an amplifier used in an integrator circuit or limited input range of measuring systems or analog to digital converter.

In another embodiment, a high performance amplifier with a small input bias current and operating from low supply voltages may be combined with an instrumentation amplifier operating from higher supply voltages adding offset to allow a wide dynamic range.

Embodiments of detectors including capacitive transimpedance amplifiers may avoid or reduce thermal noise, providing a low noise signal.

While reference is made to amplifiers and amplification elements, it is not intended that an amplifier or an amplification element be limited to a single element. Instead, it is envisioned that these terms may in some embodiments encompass circuits including multiple elements, integrated circuits, or any other arrangement suitable for amplification.

While the integrated capacitive detector is described above in combination with a particular embodiment of an IMS, it is envisioned that embodiments of the integrated capacitive detector will be utilized with various different spectrometer arrangements, including FAIMS and DMS. Exemplary spectrometry apparatus with which it is envisioned that embodiments of integrated capacitive detectors may be used are disclosed, for example, in U.S. Pat. No. 6,051,832 to Bradshaw et al., U.S. Pat. No. 6,255,623 to Turner et al., U.S. Pat. No. 5,952,652 to Taylor et al., U.S. Pat. No. 4,551,624 to Spangler et al., U.S. Pat. No. 6,459,079 to Machlinski et al., and U.S. Pat. No. 6,495,824 to Atkinson, the disclosure of each of which is incorporated herein, in its entirety, by reference.

The use of the terms "a" and an and the and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In additional embodiments, a variety of analytical devices may make use of the structures, techniques, approaches, and so on described herein. Thus, although an IMS device is described throughout this document, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on. For example, the corona source can also be used in other types of spectrometry involving an ionization process such as mass spectrometers ("MS").

Although this disclosure has described embodiments in a structural manner, the structure and its structural and/or functional equivalents can perform methods.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

What is claimed is:

1. A spectrometer comprising:
   a detector including:
   a collector configured to detect ions;
   a capacitive transimpedance amplifier coupled to the collector; and
   an offset circuit coupled to the capacitive transimpedance amplifier included in the detector.

2. The spectrometer of claim 1, wherein the offset circuit comprises a variable amplification amplifier.

3. The spectrometer of claim 2, further comprising a control circuit configured to modulate the variable amplification amplifier's amplification.

4. The spectrometer of claim 3, wherein the control circuit comprises a processor;
   wherein the control circuit is coupled with the output of the capacitive transimpedance amplifier; and wherein the control circuit modulates the amplification of the variable amplification amplifier based on the output of the capacitive transimpedance amplifier.

5. The spectrometer of claim 1, comprising an analog-to-digital converter coupled with the output of the detector, a control circuit including a processor coupled with the analog-to-digital converter, and a digital-to-analog converter coupled with the processor and with the variable amplification amplifier, wherein the control circuit is configured to control the amplification of the variable amplification amplifier to maintain the output of the detector within the dynamic range of the capacitive transimpedance amplifier and the analog-to-digital converter.

6. The spectrometer of claim 1, wherein the collector is configured as one of the plates of a feedback capacitor of the capacitive transimpedance amplifier.

7. The spectrometer of claim 1, wherein the capacitive transimpedance amplifier includes an operational amplifier with a capacitor configured in a feedback loop of the operational amplifier.

8. The spectrometer of claim 7 wherein the collector and the capacitor are coupled at a summing junction;
   wherein the summing junction is coupled with an input of the operational amplifier; and
   wherein no other components are directly coupled with the summing junction.

9. The spectrometer of claim 1, wherein the capacitive transimpedance amplifier is configured as an integrator configured to integrate ion current from the collector as a voltage.

10. The spectrometer of claim 9, wherein the capacitor is configured in a feedback loop of the amplifier so the amplifier and the capacitor are configured to convert a signal from the collector to a voltage.

11. The spectrometer of claim 1, further comprising a second collector coupled with a second transimpedance amplifier configured to receive ions at least until an ion peak has passed.

12. A spectrometer comprising:
    a detector comprising:
    an amplifier including an input and an output, the output being coupled with a capacitor;
    a collector coupled with the input of the amplifier configured to collect ions that contact the collector; and
    an offset circuit coupled with the amplifier.

13. The spectrometer of claim 12, wherein the offset circuit is configured to selectively offset the output of the amplifier.

14. The spectrometer of claim 12, wherein the offset circuit is configured to selectively offset the output of the amplifier to maintain the output of the amplifier within the dynamic range of the amplifier.

15. The spectrometer of claim 12, wherein the offset circuit includes a selectively adjustable amplifier configured in the feedback loop of the amplifier.

16. A spectrometer comprising:
    a collector configured to receive ions in the spectrometer coupled with a summing junction;
    the summing junction coupled to an input of an amplifier, the amplifier including an output;
    an offset circuit including an input and an output, the input being coupled with the output of the amplifier; and
    a capacitor coupled with output of the offset circuit and with the summing junction.

17. The spectrometer of claim 16, wherein the amplifier comprises an operational amplifier, wherein the offset circuit includes a selectively adjustable instrumentation amplifier.

18. The spectrometer of claim 17, further comprising a microprocessor configured to adjust the amplification of the instrumentation amplifier.

19. The spectrometer of any of claim 16, wherein the amplifier and capacitor are arranged to form a capacitive transimpedance amplifier, wherein the capacitor, the collector, and the amplifier are the only components electrically coupled with the summing junction.

20. The spectrometer of any of claim 16, wherein the spectrometer comprises an ion mobility spectrometer configured to operate substantially at ambient pressure.

* * * * *